(12) United States Patent
Johansson et al.

(10) Patent No.: US 6,747,156 B2
(45) Date of Patent: Jun. 8, 2004

(54) METHOD OF PRODUCING 6-SUBSTITUTED (S)-NICOTINE DERIVATIVES AND INTERMEDIATE COMPOUNDS

(75) Inventors: Anette Johansson, Indianapolis, IN (US); Torgny Svensson, Lidingö (SE)

(73) Assignee: Independent Pharmaceutica AB, Taby (SE)

( * ) Notice: Subject to any disclaimer, the term of this patent is extended or adjusted under 35 U.S.C. 154(b) by 0 days.

(21) Appl. No.: 10/221,175

(22) PCT Filed: Mar. 21, 2001

(86) PCT No.: PCT/SE01/00599
§ 371 (c)(1),
(2), (4) Date: Dec. 4, 2002

(87) PCT Pub. No.: WO01/70730
PCT Pub. Date: Sep. 27, 2001

(65) Prior Publication Data
US 2003/0187270 A1 Oct. 2, 2003

(30) Foreign Application Priority Data
Mar. 21, 2000 (SE) .............................................. 0000933

(51) Int. Cl.[7] .............................................. C07D 401/04
(52) U.S. Cl. .................................................. 546/276.4
(58) Field of Search ...................................... 546/276.4

(56) References Cited

U.S. PATENT DOCUMENTS

| 4,155,909 A | 5/1979 | Sanders et al. |
| 5,502,194 A | 3/1996 | Rivadeneira et al. |

FOREIGN PATENT DOCUMENTS

| WO | 0050428 A1 | 4/1982 |
| WO | 0439745 A2 | 8/1991 |
| WO | 0463464 A1 | 1/1992 |
| WO | WO 9961054 A1 | 12/1999 |

OTHER PUBLICATIONS

J. Org. Chem, vol. 50, 1985, Dick A. de Bie et al., "On the Amination of Halogenonitropyridines", pp. 484–487.

Primary Examiner—Patricia L. Morris
(74) Attorney, Agent, or Firm—Bacon & Thomas

(57) ABSTRACT

A method of producing a 6-substituted (S)-nicotine derivative with the general formula (III), wherein R is an optionally substituted alkyl, alkenyl, alkynyl, amido or amino group, optionally coupled to a carrier protein, is disclosed. An intermediate compound useful in the method is also comprised by the invention. The formula of the compound is (A) in which A represents the cationic radical of an organic nitrogen base, Y represents an anion formed by an electrophilic compound.

5 Claims, No Drawings

METHOD OF PRODUCING 6-SUBSTITUTED (S)-NICOTINE DERIVATIVES AND INTERMEDIATE COMPOUNDS

The present invention relates to a method of producing enantiomerically pure 6-substituted (S)-nicotine derivatives and to new intermediate compounds for use in said method.

BACKGROUND OF THE INVENTION

There are several patent applications and published articles directed to vaccines/immunogens against nicotine dependency/harm reduction, but no such vaccines/immunogens are yet on the market.

One approach is directed to a vaccine/immunogen that in an individual can elicit antibodies which strongly bind to administered/inhaled nicotine and block its effect before it reaches the central nervous system. The desired result is that the individual will not experience the expected stimulating effect of nicotine administration/smoking, and therefore the interest in administering a tobacco product, such as moist snuff, or lighting a cigarette will cease (extinction/prevention).

A complementary approach is directed to an immunogen that in an individual can elicit antibodies which moderately or weakly bind to administered/inhaled nicotine and enhance/prolong its effect in the central nervous system. The desired result is that the individual will experience the expected stimulating effect of nicotine administration/smoking during a prolonged period of time, and therefore the interest in a renewed administration of a tobacco product, such as moist snuff, or lighting a cigarette will be postponed and the medical consequences of the tobacco product consumption will be reduced.

Both of the above mentioned approaches use immunogens which in an individual induces an immunological response which leads to harm reduction.

Papers disclosing active immunization to alter nicotine distribution was recently published (Hieda Y. et al, J. Pharmacol. Exp. Therap. 1997, 283, 1076–1081, Pentel, P. R. et al, Pharmacol. Biochem. Behav. 2000, 65, 191–198). The immunogens used in the Hieda and Pentel articles were (±)-6-(carboxymethyl-ureido)-nicotine conjugated to keyhole limpet hemocyanin and (±)-trans-3'-aminomethylnicotine conjugated to *Pseudomonas aerigunosa* exoprotein A via a succinic acid linker, respectively.

The international patent application WO 98/14216 claims a large number of hapten-carrier conjugates based on the nicotine molecule and the common structural feature of the compounds seems to be that all of the hapten molecules contain a terminal carboxylic acid group which is then conjugated to the carrier. No in vivo testing has been disclosed for the alleged drug abuse treatment.

Other nicotine derivatives useful in vaccines/immunogens are comprised by the present inventors' International patent application WO9961054A1 directed to nicotine immunogens comprising 5- or 6-nicotinyl-linker-carrier proteins.

All the published 6-nicotine derivatives are produced as racemates, and if an enantiomer is desired, the production is accomplished by procedures for separating racemic mixtures into optically pure fractions well known in the art (see for example U.S. Pat. No. 5,420,286) giving ≦50% of each enantiomer.

However, it should be noted that all tobacco products contain the (S)-nicotine enantiomer only. Therefore, it is desirable to use enantiomerically pure (S)-nicotine derivatives in the different prophylactic and therapeutic applications.

DESCRIPTION OF THE INVENTION

The present invention provides a new method of producing enantiomerically pure 6-substituted (S)-nicotine derivatives in good yields and high enantiomeric purity and new intermediate compounds for use in said method.

More specifically, the present invention is directed to a method of producing a 6-substituted (S)-nicotine derivative with the general formula (III),

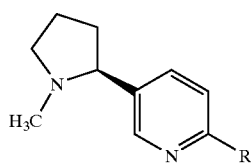

(III)

wherein R is an optionally substituted alkyl, alkenyl, alkynyl, amido or amino group.

The method comprises the steps of a) reacting (S)-nicotine-N1-oxide with an organic nitrogen base A, selected from trialkylamine, dialkylbenzylamine, dialkylcyclohexylamine and pyridine in which the alkyl groups may be individually selected from lower alkyl groups, and an electrophilic compound, if appropriate in the presence of a organic solvent to produce a (S)-nicotine derivative with the general formula

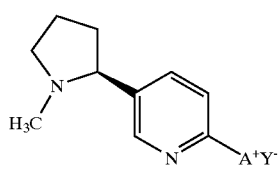

(I)

wherein
A represents a cationic radical of the organic nitrogen base, and
Y represents an anion formed by the electrophilic compound, b) reacting the compound (I) with a nucleophilic reagent to produce the (S)-nicotine derivative with the general formula

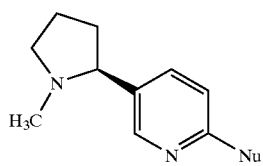

(II)

wherein Nu represents the nucleophile, and reacting the compound (II) with an optionally substituted alkyn to produce a 6-substituted (S)-nicotine derivative with the formula (III) wherein R is an optionally substituted alkyn group, followed by the optional steps of hydrogenation of the triple bond of the alkyne to produce a compound with the formula (III) wherein R is an alkyl or alkenyl group or reacting the compound (II) with an amide anion to produce (S)-6-aminonicotine which then is coupled with an optionally substituted carboxylic acid to produce a 6-substituted (S)-nicotine derivative with the formula (III) wherein R is an optionally substituted amido group followed by the optional step of reduction of the amide to produce a compound with the formula (III) wherein R is an amino group.

In a preferred embodiment the produced compounds are those wherein the substituent R is

—X—Y—Z-Q wherein

X is —NH—CO— or —NH— or —C≡C— or —C≡C—
or —CH$_2$—;
Y is —(CH$_2$)$_k$— or (CH$_2$)$_m$—C$_6$H$_{10}$(CH$_2$)$_n$— or (CH$_2$)$_m$—
C$_6$H$_4$—(CH$_2$)$_n$—
wherein k=0–20, m=0–6, and n=0–6, when
Z is —NH— and Q is H
and
X is —NH—CO— or —C≡C— or —C=C— or
—CH$_2$—,
Y is —(CH$_2$)$_m$—C$_6$H$_{10}$—(CH$_2$)$_n$— or (CH$_2$)$_m$—C$_6$H$_4$(CH$_2$)$_n$—
wherein m=0–6, and n=0–6, when
Z is —CO— and Q is —OH
and
X is —C≡C— or —C=C—,
Z is —CO— and Q is —OH, when
Y is —(CH$_2$)$_k$—
wherein k=0–20.

These compounds are, in racemic form, comprised by our earlier international patent application WO 9961054.

In another preferred embodiment A represents an organic nitrogen base selected from the group consisting of: trialkylamine, dialkylbenzylamine, dialkylcyclohexylamine and pyridine in which the alkyl groups may be individually selected from lower alkyl groups, and Y represents an arylsulphonate ion, a chloride ion or a lower alkylcarboxylate ion.

In a most preferred embodiment A represents trimethylamine, triethylamine, tripropylamine, tributylamine, N,N-dimethylbenzylamine, N,N-diethylbenzylamine, N,N-dimethylcyclohexylamine and N,N-diethylcyclohexylamine, and Y represents a benzenesulphonate ion, a chloride ion or an acetate ion.

In yet another embodiment of the method off the invention the nucleophilic reagent is selected from the group consisting of halogenating agents.

The present invention is also directed to the intermediate compound of the formula

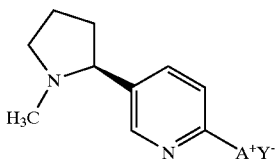

(I)

in which

A represents the cationic radical of an organic nitrogen base

Y represents an anion formed by an electrophilic compound.

Also in this aspect of the invention A preferably represents an organic nitrogen base selected from the group consisting of: trialkylamine, dialkylbenzylamine, dialkylcyclohexylamine and pyridine, in which the alkyl groups may be individually selected from lower alkyl groups, and Y represents an arylsulphonate ion, a chloride ion or a lower alkylcarboxylate ion. Most preferably A represents trimethylamine, triethylamine, tripropylamine, tributylamine, N,N-dimethylbenzylamine, N,N-diethylbenzylamine, N,N-dimethylcyclohexylamine and N,N-diethylcyclohexylamine, and Y represents a benzenesulphonate ion, a chloride ion or an acetate ion.

The 6-substituted (S)-nicotine derivatives produced by the method of the invention may be coupled to carrier proteins in the same way as disclosed in our international patent application WO 9961054. Examples of suitable carrier proteins are keyhole limpet hemocyanin (KLH), tetanus toxoid, diphtheria toxoid, non-toxic mutant diphtheria toxoid CRM$_{197}$, outer membrane protein complex (OMPC) from *Neisseria meningitidis*, the B subunit of heat-labile *Escherichia coli*, and recombinant exoprotein A from *Pseudomonas aeruginosa* (rEPA).

The 6-substituted (S)-nicotine derivatives produced by the method of the invention coupled to carrier proteins will find use as vaccines/immunogens for prophylactic and/or therapeutic immunological treatment of nicotine dependence from tobacco products to achieve harm reduction in an individual.

The present invention will now be further illustrated by reference to the following description of synthesis of typical examples of intermediate compounds and end products. However, these illustrated embodiments are not to be considered as limitations to the scope of the invention defined in the claims.

Description of Synthesis of Compounds

The starting material for the synthesis, (S)-nicotine mono-N1-oxide, is obtained from (S)-nicotine as previously described in the literature, and all the other chemicals used in the illustrated syntheses are either bought or synthesized as previously described in our international patent application WO 9961054.

In the following Scheme 1 the synthetic pathway for producing the compounds of the structural formulae (I)–(III) is illustrated with exemplary compounds. The 6-substituted (S)-nicotine compounds 5–10 are disclosed, as racemates, in our international patent application WO 9961054.

Scheme 1

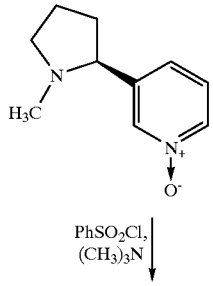

PhSO$_2$Cl,
(CH$_3$)$_3$N

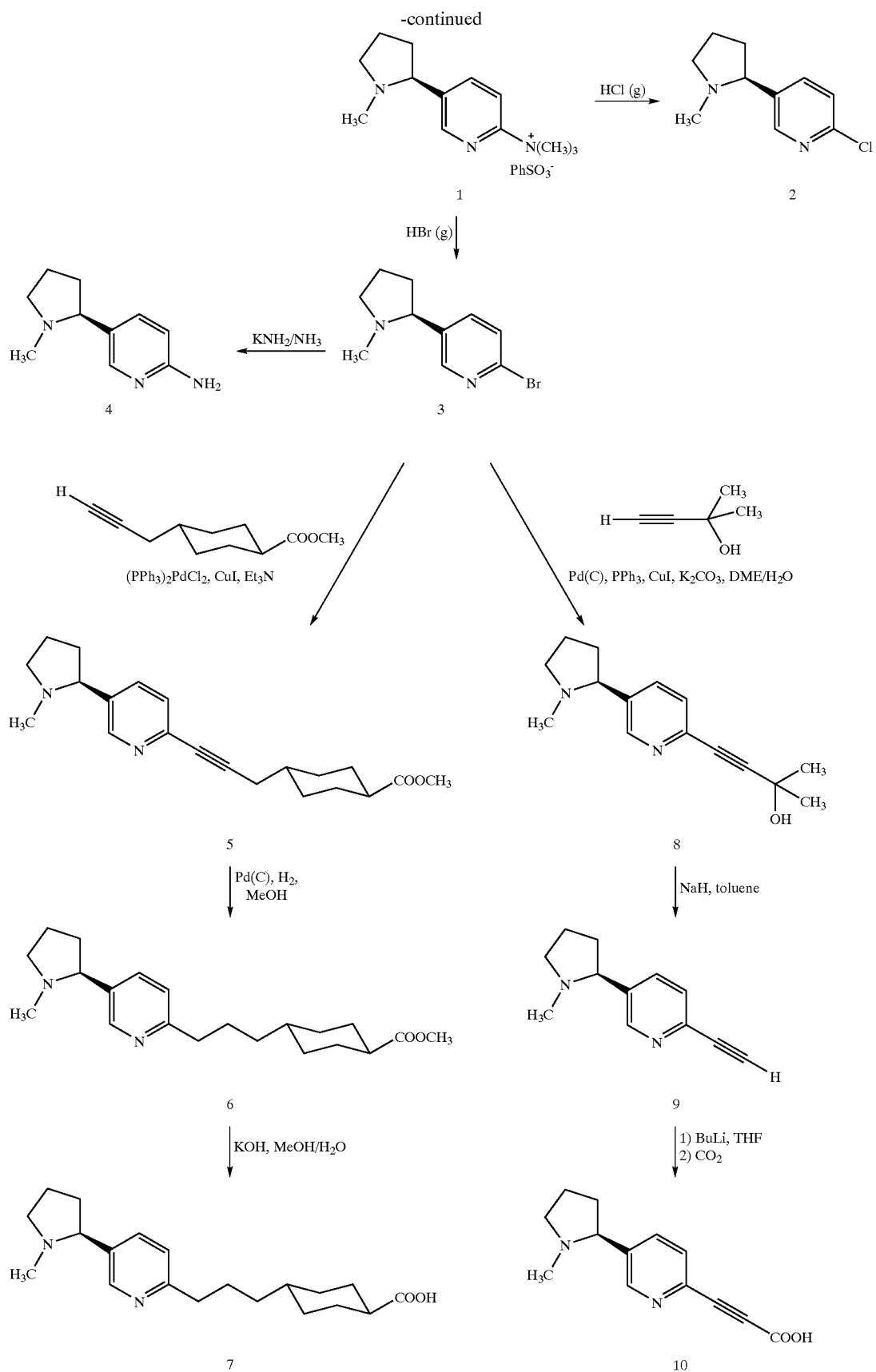

(S)-Trimethyl-[5-(1-methyl-pyrrolidin-2-yl)-pyridin-2-yl] ammonium Benzenesulfonate (1).

Trimethylamine (5.9 g, 0.1 mol) was condensed at −25° C. into a stirred solution of (S)-nicotine mono-N1-oxide[1] (1.77 g, 0.01 mol) in dry $CH_2Cl_2$ (20 mL). A solution of benzenesulfonyl chloride (3.7 g, 0.02 mol) in dry $CH_2Cl_2$ (15 mL) was added dropwise at −15° C., over a period of 60 min. The mixture was stirred at this temperature for 60 min and then allowed to reach room temperature. After 3 h at room temperature, the reaction mixture was concentrated in vacuo. The residue was treated with $CH_2Cl_2$ (50 mL) and most of the trimethylamine hydrochloride was filtered off and the solution was concentrated in vacuo. The residue was purified by flash chromatography [$Al_2O_3$, $CHCl_3$, then $CHCl_3$/MeOH, (15:1)], to yield 2.86 g (76%) of product. An analytical sample was obtained by crystallization from MeOH/benzene.

[1]Taylor, E. C. and Boyer, N. E. *J. Org. Chem.* 1959, 24, 275–277.

Anal. Calcd. for $C_{19}H_{27}N_3SO_3 \cdot 0.25H_2O$: C, 59.7; H, 7.3; N, 11.0. Found: C, 59.7; H, 7.2; N, 10.9; mp (MeOH/benzene): 149.0–151.0° C. (dec); $[\alpha]_D^{rt}$ −60.0° [c 0.9, MeOH]

$^1$H NMR (270 MHz, $CDCl_3$): δ 8.46 (br s, 1H); 8.25 (d, J=8.5 Hz, 1H); 7.88 (m, 3H); 7.33 (m, 3H); 3.84 (s, 9H); 3.27 (br t, J=7.5 Hz, 2H); 2.40 (dd, J=17.5, 8.5 Hz, 1H); 2.24 (m, 4H); 1.89 (m, 2H); 1.66 (m, 1H). $^{13}$C NMR (68 MHz, $CDCl_3$): δ 156.2, 148.2, 146.7, 140.7, 2×129.6, 2×128.3, 126.1, 115.4, 67.9, 56.9, 3×55.5, 40.2, 35.1, 22.8, 1.2.

(S)-6-Chloronicotine (2)[2].

[2]Roduit, J. P.; Wellig, A.; Kiener, A. *Heterocycles*, 1997, 45, 1687–1702.

A solution of 1 (130 mg, 0.3 mmol) in dry 1,2-dichloroethane (10 mL) was saturated with HCl (g), and the reaction mixture was stirred at 35° C. for 22 h. The solvent was evaporated in vacuo. The residue was dissolved in $CH_2Cl_2$ and the pH of the mixture was brought to pH~7–8 by addition of saturated aq $NaHCO_3$. The organic layer was washed with brine, dried ($MgSO_4$), filtered and concentrated in vacuo to yield a brownish oil. The oil was chromatographed [$Al_2O_3$, iso-hexane/AcOEt, (4:1)] to afford 53.3 mg (78%) of 2 as a pink oil. $[\alpha]_D^{23}$ −154.3° (c 1.0 MeCN) [lit.[2] $[\alpha]_D^{23}$ −154° (c 1.0 MeCN)].

(S)-6-Bromonicotine (3).

A solution of 1 (1.1 g, 2.9 mmol) in dry $CH_2Cl_2$ (50 mL) was saturated with HBr [(g) dried with $Mg(ClO_4)_2$], and the reaction mixture was stirred at ambient temperature for 30 h. The solvent was evaporated in vacuo. The residue was dissolved in $CH_2Cl_2$ and the pH of the mixture was brought to pH~7–8 by addition of saturated aq $NaHCO_3$. The organic layer was washed with brine, dried ($MgSO_4$), filtered and concentrated in vacuo to yield a brownish oil. The residue was chromatographed [$Al_2O_3$, iso-hexane/AcOEt (4:1)] to afford 0.53 g (75%) of 3 as a colorless oil (turns reddish with time).

3: $^1$H NMR (270 MHz, $CDCl_3$): δ 8.27 (d, 1H; J=2.5 Hz); 7.57 (dd, 1H; J=8.3, 2.5 Hz); 7.42 (dd, 1H; J 8.6, 0.3 Hz); 3.21 (ddd, 1H; J=8.6, 8.6, 2.2 Hz); 3.06 (brt, 1H; J=8.3 Hz); 2.30 (dd, 1H; J=17.6, 9.2 Hz); 1.88 (m, 2H); 2.18 (m, 4H); 1.66 (m, 1H). $^{13}$C NMR (68 MHz, $CDCl_3$): δ 149.6, 140.5, 138.4, 137.8, 128.0, 67.9, 56.8, 40.2, 35.2, 22.6.

MS (EI, 70 eV) m/z 240; 242 (1:1) (M$^+$); $[\alpha]_D^{rt}$ −132.5° (c 1, $CH_3CN$); The enantiomeric purity was determined by chiral HPLC.

Treatment of 3 with picric acid in $EtOH:H_2O$ yielded the monopicrate salt 3 monopicrate: mp ($EtOH/H_2O$) 141.0–143.0° C.

Anal. Calcd. for $C_{16}H_{16}N_5O_7Br$: C, 40.9; H, 3.4; N, 14.9. Found: C, 40.4; H, 3.4; N, 14.7.

3 monopicrate salt: $^1$H NMR (270 MHz, $CD_3COCD_3$): δ 8.75 (s, 2H); 8.61 (d, 1H; J=2.6 Hz); 8.15 (dd, 1H, J=8.4, 2.6 Hz); 7.64 (d, 1H; J=8.4 Hz); 4.68 (brs, 1H); 4.08 (br s, 1H); 3.57 (m, 1H); 3.03 (s, 3H); 2.54 (m, 4H). $^{13}$C NMR (68 MHz, $CD_3COCD_3$): δ 162.5, 152.3, 144.3, 142.9, 2×140.3, 129.5, 128.4, 2×126.5, 70.8, 57.6, 39.8, 31.7, 22.4.

(S)-6-Aminonicotine (4)[3].

[3]Gol'dfarb, Ya. L. and Smorgonskii, L. M. *Izvest. Akad. Nauk S.S.S.R. Otdel. Khim. Nauk* 1946, 557.

Potassium metal (78 mg, 2 mmol) was added to ~15 mL of $NH_3$ followed by 5–10 mg of $Fe(NO_3)_3 \cdot 9H_2O$ to catalyze amide formation. After the potassium amide had formed (gray suspension), a solution of 3 (120 mg, 0.5 mmol) in dry ether (5 mL) was added. The mixture was stirred for 20 min and quenched with excess of solid $NH_4Cl$. Ammonia was evaporated and the solid residue was treated with saturated aq. $K_2CO_3$ and extracted with ether (5×5 mL). The combined ether extracts was dried with KOH and then evaporated. The residue was purified by column chromatography [silica, $CHCl_3$/MeOH saturated with ammonia, (20:1)] to give 54 mg (61%) of 4: mp 66–67° C.; $[\alpha]_D^{rt}$=−120.1 (c 1, MeOH).

4: $^1$H NMR (270 MHz, $CDCl_3$): δ 7.95 (d, 1H; J=2.0 Hz); 7.5 (dd, 1H; J=8.4; 2.3 Hz); 6.51 (d, 1H; J 8.4 Hz); 4.44 (brs, 2H); 3.22 (ddd, 1H; J=9.6, 9.6, 2.0 Hz); 2.94 (brt, 1H; J=8.3 Hz); 2.25 (dd, 1H; J=17.5, 9.1 Hz); 2.09 (m, 4H); 1.94 (m, 1H); 1.76 (m, 2H).

$^{13}$C NMR (68 MHz, $CDCl_3$) δ 158.1, 147.4, 137.2, 128.2, 109.1, 68.7, 57.0, 40.3, 34.7, 22.4.

MS (EI, 70 eV) m/z 177 (M+). The enantiomeric purity was determined by chiral HPLC.

(S)-trans-4-[3-(5-(1-Methyl-2-pyrrolidinyl)-2-pyridinyl) prop-2-ynyl]cyclohexanecarboxylic Acid Methyl Ester (5).

A mixture of 3 (0.2 g, 0.8 mmol), bis(triphenylphosphine) palladium dichloride (0.014 g, 0.02 mmol) and CuI (0.004 g, 0.02 mmol) in 5 mL of $Et_3N$ was deoxygenated with $N_2$. trans-4-Prop-2-ynylcyclohexancarboxylic acid methyl ester[4] (0.2 g, 1.1 mmol) was added and the reaction mixture was heated at 120° C. for 45 min in a sealed vessel. The $Et_3N$ was evaporated in vacuo and the residue was dissolved in EtOAc, washed with saturated aqueous $NaHCO_3$ and extracted with 2×15 mL of 2N HCl. The acidic aqueous phase was extracted with EtOAc (3×20 mL). The aqueous layer was saturated with solid $NaHCO_3$ and extracted with EtOAc (3×20 mL). The organic phase was washed with brine, dried ($Na_2SO_4$), filtered and concentrated in vacuo. The residue was chromatographed [silica, acetone/iso-hexane (1:2)] to yield 0.26 g (93%) of 5.

[4]Svensson, T. and Johansson, A. WO9961054A1, 1999.

IR (film) $\nu_{max}$ 2226 cm$^{-1}$. $^1$H NMR ($CDCl_3$, 270 MHz) δ 8.40 (br s, 1H), 7.63 (dd, J=8.1; 2.0 Hz, 1H), 7.30 (d, J=8.1 Hz, 1H), 3.60 (s, 3H), 3.25–3.18 (m, 1H), 3.08 (app t, 1H), 2.31–2.08 (m, 5H), 2.12 (s, 3H), 1.98–1.32 (m, 10H), 1.15–0.99 (m, 2H); $^{13}$C NMR ($CDCl_3$, 68 MHz) δ 176.4, 149.6, 142.8, 137.2, 135.1, 126.9, 89.0, 81.6, 68.8, 56.9, 51.6, 43.0, 40.2, 36.5, 35.0, 31.7, 28.8, 26.8, 22.6. MS (EI, 70 eV) m/z 340 (M$^+$) Anal. Calcd. for $C_{21}H_{28}N_2O_2$: C, 74.09; H, 8.29; N, 8.23%. Found: C, 73.84; H, 8.27; N, 8.32%.

$[\alpha]_D^{rt}$=−84.0 (c 1, MeOH)

(S)-trans-4-[3-(5-(1-Methyl-2-pyrrolidinyl)-2-pyridinyl) propyl]cyclohexanecarboxylic Acid Methyl Ester (6).

A solution of 5 (0.13 g, 0.4 mmol) in MeOH (40 mL) was hydrogenated at room temperature and atmospheric pressure over 10% Pd/C (0.06 g). After 40 min the catalyst was filtered off and washed with MeOH. The volatiles was evaporated under reduced pressure and the residue was chromatographed [$SiO_2$, acetone/iso-hexane (1:2)] to afford 0.13 g (93%) of 6.

$^1$H NMR (CDCl$_3$, 270 MHz) δ 8.39 (d, J=2.0 Hz, 1H), 7.67 (dd, J=7.9; 1.8 Hz, 1H), 7.10 (d, J=7.9 Hz, 1H), 3.62 (s, 3H), 3.31–3.25 (m, 1H), 3.12 (app t, 1H), 2.72 (t, J=7.7 Hz, 2H), 2.39–2.12 (m, 2H), 2.18 (s, 3H), 2.02–1.65 (m, 9H), 1.44–1.29 (m, 2H), 1.30–1.22 (m, 3H), 0.96–0.80 (m, 2H); $^{13}$C NMR (CDCl$_3$, 68 MHz) δ 176.8, 161.8, 149.1, 135.5, 134.6, 122.9, 69.0, 57.0, 51.6, 43.6, 40.2, 38.5, 37.1, 37.0, 34.8, 32.4, 29.1, 27.4, 22.5. MS (EI, 70 eV) m/z 344 (M$^+$) Anal. Calcd. for C$_{21}$H$_{32}$N$_2$O$_2$x0.2H$_2$O: C, 72.46; H, 9.37; N, 8.05%. Found: C, 72.34; H, 9.44; N, 8.06%; [α]$_D^{rt}$=–61.0 (c 1, MeOH).

(S)-trans-4-[3-(5-(1-Methyl-2-pyrrolidinyl)-2-pyridinyl)propyl]cyclohexanecarboxylic Acid (7).

A mixture of 6 (0.11 g, 0.3 mmol) and KOH (0.025 g, 0.45 mmol) in 50% aqueous MeOH (10 mL) was heated under reflux for 30 min. The reaction mixture was acidified with HOAc to pH 8 and the solvents were evaporated in vacuo. The crude product was purified by column chromatography (silica gel, CHCl$_3$/MeOH, gradient of MeOH 10% to 50%) to afford 0.077 g (74%) of 7.

$^1$H NMR (CD$_3$OD, 270 MHz) δ 8.44 (br s, 1H), 7.83 (dd, J=8.1; 2.2 Hz, 1H), 7.34 (d, J=8.1 Hz, 1H), 3.50 (app t, 1H), 3.43–3.35 (m, 1H), 2.77 (t, 7.7 Hz, 2H), 2.66–2.56 (m, 1H), 2.40–2.26 (m, 1H), 2.31 (s, 3H), 2.11–1.67 (m, 10H), 1.45–1.23 (m, 5H), 0.98–0.86 (m, 2H); $^{13}$C NMR (CDCl$_3$, 68 MHz) δ 184.0, 163.5, 149.6, 138.1, 134.6, 124.8, 70.3, 57.7, 40.2, 38.8, 38.5, 38.2, 34.7, 33.9, 31.0, 28.6, 23.2; [α]$_D^{rt}$=–49.0 (c 2, MeOH).

(S)-2-(3-Hydroxy-3-methylbut-1-ynyl)-5-(1-methyl-2-pyrrolidinyl)pyridine (8).

A mixture of 3 (0.2 g, 0.8 mmol), triphenylphosphine (0.022 g, 0.08 mmol), 10% Pd/C (0.022 g, 0.021 mmol in Pd), CuI (0.016 g, 0.08 mmol) and K$_2$CO$_3$ (0.24 g, 2.0 mmol) in 30 mL of a mixture DME/H$_2$O (1:1) was deoxygenated with N$_2$. The mixture was stirred at room temperature for 30 min and then 2-methyl-3-butyn-2-ol (0.17 g, 2.0 mmol) was added. After stirring under reflux for 7 h the mixture was filtered over a celite pad and concentrated in vacuo to half the volume. The residue was made acidic with 2M HCl and then washed with toluene (2×10 mL). The aqueous phase was saturated with K$_2$CO$_3$ and extracted with EtOAc (3×20 mL), washed with brine, dried over Na$_2$SO$_4$ and concentrated in vacuo. The residue was purified by column chromatography [silica gel, iso-hexane/acetone (1:1)] to give 0.131 g (66%) of 8.

IR (film) ν$_{max}$ 2238 cm$^{-1}$. $^1$H NMR (CDCl$_3$, 270 MHz) δ 8.43 (br s, 1H), 7.65 (dd, J=8.0; 2.1 Hz, 1H), 7.33 (d, J=8.1 Hz, 1H), 4.05 (br s, 1H), 3.23–3.16 (m, 1H), 3.05 (app t, 1H), 2.31–2.21 (m, 1H), 2.18–2.07 (m, 1H), 2.11 (s, 3H), 1.94–1.60 (m, 3H), 1.64 (s, 6H); $^{13}$C NMR (CDCl$_3$, 68 MHz) δ 149.6, 141.9, 138.2, 135.4, 127.2, 94.5, 81.2, 68.8, 65.0, 57.1, 40.5, 35.2, 31.4, 22.6. MS (EI, 70 eV) m/z 244 (M$^+$) Anal. Calcd. for C$_{15}$H$_{20}$N$_2$O: C, 73.74; H, 8.25; N, 11.46%. Found: C, 73.56; H, 8.36; N, 11.40%; [α]$_D^{rt}$=–172.0 (c 1, MeOH).

(S)-2-Ethynyl-5-(1-methyl-2-pyrrolidinyl)pyridine (9).

Compound 8 (0.12 g, 0.5 mmol) and NaH as a 60% dispersion in mineral oil (0.005 g, 0.13 mmol) were dissolved in dry toluene (10 mL). The stirred solution was slowly distilled until the boiling point of the distillate reached 110° C. The rest of the toluene was evaporated in vacuo. The residue was chromatographed [SiO$_2$, CHCl$_3$/MeOH, (10:1)] to give 0.062 g, (67%) of 9 as a yellow oil.

$^1$H NMR (CDCl$_3$, 270 MHz) δ 8.49 (d, J=2.2 Hz, 1H), 7.67 (dd, J=8.0; 2.1 Hz, 1H), 7.43 (d, J=7.9 Hz, 1H), 3.25–3.18 (m, 1H), 3.11–3.03 (m, 2H), 2.34–2.24 (m, 1H), 2.23–2.09 (m, 1H), 2.14 (s, 3H), 1.98–1.60 (m, 3H); $^{13}$C NMR (CDCl$_3$, 68 MHz) δ 149.9, 141.2, 139.2, 135.2, 127.5, 83.0, 76.9, 68.8, 57.1, 40.5, 35.4, 22.8. MS (EI, 70 eV) m/z 186 (M$^+$) Anal. Calcd. for C$_{12}$H$_{14}$N$_2$: C, 77.39; H, 7.58; N, 15.04%. Found: C, 77.29; H, 7.44; N, 14.89%; [α]$_D^{rt}$=–148.5 (c 1, MeOH).

(S)5-(1-Methyl-2-pyrrolidinyl)-2-pyridinylpropiolic Acid (10).

A solution of 9 (0.053 g, 0.3 mmol) in THF (8 mL) was cooled to –78° C. and BuLi (1.6M solution in hexane, 0.2 mL, 0.32 mmol) was added. The reaction mixture was stirred for 0.5 h at –78° C. and then CO$_2$ gas was added. After an additional 1 h at –78° C. the reaction mixture was allowed to warm to room temperature. THF was evaporated in vacuo and the residue was purified by column chromatography [silica gel, CHCl$_3$/MeOH, (1:1)]; yield 0.04 g, (87% based on recovered 9) of 10.

$^1$H NMR (CD$_3$OD, 270 MHz) δ 8.48 (d, J=1.8 Hz, 1H), 7.84 (dd, J=8.1; 2.2 Hz, 1H), 7.59 (d, J=8.1 Hz, 1H), 3.28–3.20 (m, 2H), 2.44–2.39 (m, 1H), 2.31–2.21 (m, 1H), 2.18 (s, 3H), 2.01–1.68 (m, 3H); $^{13}$C NMR (CD$_3$OD, 68 MHz) δ 160.6, 150.6, 142.4, 140.3, 137.6, 129.2, 87.2, 78.3, 70.0, 58.0, 40.8, 35.9, 23.5; [α]$_D^{rt}$=–42.0 (c 0.5, MeOH).

What is claimed is:

1. A method of producing a 6-substituted (S)-nicotine derivative with the formula (III),

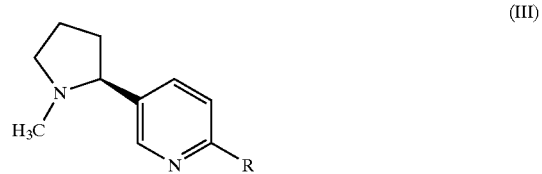

(III)

wherein R is an optionally substituted alkyl, alkenyl, alkynyl, selected from the group consisting of —X—Y—Z—O wherein X is —C≡C— or —C=C— or —CH$_2$—;

Y is —(CH$_2$)$_k$— or —(CH$_2$)$_m$—C$_6$H$_{10}$—(CH$_2$)$_n$— or —(CH$_2$)$_m$—C$_8$H$_4$—(CH$_2$)$_n$— wherein k=0–20, m=0–6, and n=0–6, when

Z is —NH— and Q is H or a carrier protein, and

X is —C≡C— or —C=C— or —CH$_2$—,

Y is —(CH$_2$)$_m$—C$_6$H$_{10}$—(CH$_2$)$_n$— or —(CH$_2$)$_m$—C$_6$H$_4$—(CH$_2$)$_n$— wherein m=0–6, and n=0–6, when

Z is —CO— and Q is —OH or a carrier protein, and

X is —C°C— or —C=C—,

Z is —CO— and Q is —OH or a carrier protein, when

Y is —(CH$_2$)$_k$ wherein k=0–20, optionally coupled to a carrier protein, comprising the steps of a) reacting (S)-nicotine-N1-oxide with an organic nitrogen base A, selected from the grow, consisting of trialkylamine, dialkylbenzylamine, dialkylcyclohexylamine and pyridine in which the alkyl groups may be individually selected from lower alkyl groups, and an electrophilic compound selected from the group consisting of an arylsulphonate, a chloride and a lower alkylcarboxylate, optionally in the presence of an organic solvents to produce a (S)-nicotine derivative with the formula

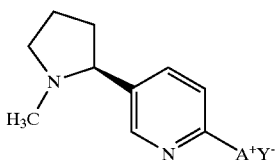

(I)

wherein A represents a cationic radical of the organic nitrogen base, and

Y represents an anion formed by the electrophilic compound, b) reacting the compound (I) with a nucleophilic reagent selected from the group consisting of halogenating agents to produce the (S)-nicotine derivative with the formula

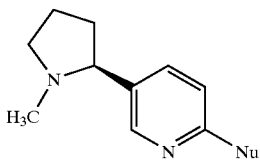

(II)

wherein Nu represents the nucleophile, and reacting the compound (II) with an optionally substituted alkyn to produce the 6-substituted (S)-nicotine derivative with the formula (III) wherein R is the optionally substituted alkyn group, followed by the optional steps of hydrogenation of the triple bond of the alkyne to produce a compound with the formula (III) wherein R is the alkyl or alkenyl group, whereupon the compound (III) is optionally coupled via the terminal carboxylic acid or amine group to a carrier protein.

2. Method according to claim 1, wherein

A represents an organic nitrogen base selected from the group consisting of:

trialkylamine, dialkylbenzylamine, dialkylcyclohexylamine and pyridine in which the alkyl groups may be individually selected from lower alkyl groups, and Y represents an arylsulphonate ion, a chloride ion or a lower alkylcarboxylate ion.

3. Method according to claim 1, wherein

A represents a group selected from the group consisting of trimethylamine, triethylamine, tripropylamine, tributylamine, , N-dimethylbenzylamine, N,N-diethylbenzylamine, N,N-dimethylcyclohexylamine and N, N-diethylcyclohexylamine.

4. Method according to claim 2, wherein the nucleophilic reagent is selected from the group consisting of halogenating agents.

5. Method according to claim 3, wherein the nucleophilic reagent is selected from the group consisting of halogenating agents.

* * * * *